United States Patent
Yee et al.

(10) Patent No.: US 7,966,861 B2
(45) Date of Patent: Jun. 28, 2011

(54) JIG FRAME FOR DROP TEST OF FLAT PANEL DISPLAY DEVICE

(75) Inventors: Dong-Su Yee, Suwon-si (KR); Kuen-Dong Ha, Suwon-si (KR); Hyun-Min Hwang, Suwon-si (KR); Chan-Kyoung Moon, Suwon-si (KR); Hyun-Hee Lee, Suwon-si (KR); Jung-Jun Im, Suwon-si (KR); Oh-June Kwon, Suwon-si (KR); Ji-Ho Kang, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 21 days.

(21) Appl. No.: 12/289,977

(22) Filed: Nov. 7, 2008

(65) Prior Publication Data
US 2009/0165532 A1    Jul. 2, 2009

(30) Foreign Application Priority Data

Dec. 27, 2007  (KR) .................. 10-2007-0139027
Jan. 9, 2008   (KR) .................. 10-2008-0002746

(51) Int. Cl.
*G01N 3/00*    (2006.01)
(52) U.S. Cl. .......................... 73/12.09; 73/856
(58) Field of Classification Search .......... 73/856, 73/12.09
See application file for complete search history.

(56) References Cited

U.S. PATENT DOCUMENTS

| | | | | |
|---|---|---|---|---|
| 5,734,158 A * | 3/1998 | Nagashima et al. | ........ | 250/225 |
| 7,242,212 B2 * | 7/2007 | Jung | ............ | 324/770 |
| 7,439,757 B2 * | 10/2008 | Kang et al. | ........ | 324/770 |
| 7,535,548 B2 * | 5/2009 | Lee | ............ | 349/192 |
| 7,570,314 B2 * | 8/2009 | Lee | ............ | 349/58 |
| 2005/0147377 A1 * | 7/2005 | Kobayashi et al. | ........ | 386/46 |
| 2007/0127144 A1 * | 6/2007 | Gao | ............ | 359/820 |
| 2009/0167171 A1 * | 7/2009 | Jung et al. | ........ | 313/504 |
| 2009/0195973 A1 * | 8/2009 | Yee et al. | ........ | 361/679.21 |
| 2009/0201458 A1 * | 8/2009 | Lee | ............ | 349/187 |

FOREIGN PATENT DOCUMENTS

| | | |
|---|---|---|
| JP | 2006-170641 | 6/2006 |
| KR | 2000-0019450 | 11/2000 |
| KR | 10-2006-0057072 | 5/2006 |
| KR | 10-2007-0002165 | 1/2007 |
| KR | 10-2007-0010858 | 1/2007 |

OTHER PUBLICATIONS

Min-Chun Pan, Drop simulation/experimental verification and shock resistance improvement of TFT-LCD monitors, 2003, IEEE.*

* cited by examiner

*Primary Examiner* — Freddie Kirkland, III
(74) *Attorney, Agent, or Firm* — Robert E. Bushnell, Esq.

(57) ABSTRACT

A jig frame for a drop test of a flat panel display, which is designed to allow a tester to effectively identify if the flat panel display is damaged and to easily adjust its weight and degree of deformation is provided. The jig frame for a drop test of a flat panel display includes a base plate having a groove for receiving the flat panel display and a cover plate fixing the flat panel display by covering the flat panel display and being coupled to the base plate. The cover plate is formed of transparent material so that the flat panel display installed in the jig frame is visible to outside of the cover plate.

18 Claims, 12 Drawing Sheets

JIG FRAME FOR DROP TEST OF FLAT PANEL DISPLAY DEVICE

CLAIM OF PRIORITY

This application claims priority to and the benefit of Korean Patent Application Nos. 10-2007-0139027 filed on Dec. 27, 2007 and 10-2008-0002746 filed on Jan. 9, 2008, in the Korean Intellectual Property Office, the entire contents of which are incorporated herein by references.

BACKGROUND OF THE INVENTION

1. Field of the Invention

The present invention relates to a jig frame for a drop test of a flat panel display. More particularly, the present invention relates to a jig frame for a drop test of a flat panel display, which is designed to allow a tester to effectively identify if the flat panel display is damaged.

2. Description of the Related Art

In recent years, slim, light-weight flat panel displays have been widely used to overcome disadvantages of cathode ray tubes. Organic light emitting diode (OLED) displays and liquid crystal displays (LCDs) are representative of the flat panel displays and are widely used as displays of mobile electronic devices such as mobile phones, personal multimedia players (PMPs), and the like.

The flat panel displays have to have proper durability that will serve their purposes. Therefore, a variety of tests for inspecting durability of the flat panel display with respect to physical external impact have been performed. A drop test is well known as one of the durability inspecting tests. In the drop test, the flat panel display is installed in a jig frame and the durability of the flat panel display is inspected by dropping the jig frame.

Particularly, when the flat panel display is applied to a mobile electronic device, the user may inadvertently drop the mobile electronic device. Therefore, the flat panel display has to have a predetermined mechanical strength withstanding the drop impact.

A typical jig frame used for the drop test includes an inner case for receiving a flat panel display and an outer case covering the inner case. At least one plate may be located between the inner and outer cases. The plate is fixed to the inner case by a plurality of bolts and the inner case is coupled to the outer case by a plurality of bolts.

The drop test is performed by dropping the jig frame that is assembled by the bolts from a predetermined height. After the drop test, the inner and outer cases are disassembled from each other by releasing the bolts, after which a tester can identify using the naked eye if the flat panel display is damaged.

That is, since the jig frame is formed of non-transparent material, the tester can identify the damage of the flat panel display only after the jig frame is disassembled. This is troublesome for the tester.

Additionally, the typical jig frame is provided in the form of a fixed structure, it is impossible to adjust its weight and degree of deformation. Therefore, the typical jig frame cannot meet a variety of conditions of the electronic device to which the flat panel display will be applied. Therefore, in order to meet the variety of the conditions of the electronic device, a new jig frame must be manufactured.

Further, since the typical jig frame is not durable, bolt coupling portions of the jig frame may be easily damaged. Furthermore, since 10 or more bolts must be coupled and released for each drop test, the drop test is time-consuming. In addition, every tester has different screw torque. This causes dispersion of the jig frame and thus deteriorates the reliability of the drop test.

The above information disclosed in this Background section is only for enhancement of understanding of the background of the invention and therefore it may contain information that does not form the prior art that is already known to a person of ordinary skill in the art.

SUMMARY OF THE INVENTION

Exemplary embodiments of the present invention provide a jig frame for a drop test of a flat panel display, which is designed to allow a tester to effectively identify if the flat panel display is damaged and reduce the drop test time.

Exemplary embodiments of the present invention also provide a jig frame for a drop test of a flat panel display, which is designed to easily adjust its weight and degree of deformation and thus to effectively meet a variety of different conditions of an electronic device to which the flat panel display will be applied.

In an exemplary embodiment of the present invention, a jig frame for a drop test of a flat panel display includes a base plate having a groove for receiving the flat panel display and a cover plate fixing the flat panel display by covering the flat panel display and being coupled to the base plate. The cover plate is formed of transparent material so that the flat panel display installed in the jig frame is visible to outside of the cover plate.

The flat panel display may include a display region and the cover plate may be provided with an opening corresponding to the display region.

The jig frame may further include at least one balance weight coupled to an edge of the base plate. The base plate may be formed in a rectangular shape and the balance weight is located at each of four corners of the base plate.

The base plate may be provided at each of the four corners with a plurality of coupling holes arranged in a length direction of the base plate and the balance weight at each of the four corners may be coupled to one of the coupling holes. Each of the coupling hole may be provided with a female thread and the balance weight is provided with a male thread so that the balance weight is screw-coupled to the coupling hole.

The balance weight may be provided on each of top and under surfaces of each of the four corners of the base plate. The balance weight provided on the top surface of the base plate may have the same weight as the balance weight provided on the undersurface of the base plate.

The cover plate may be coupled to the base plate by fitted in the base plate by sliding motion. The base plate may be formed in a rectangular shape, an opening region through which the cover plate slides into the base plate may be formed on one of four sides of the base plate, and a guide holder partly overlapping the cover plate coupled to the base plate may be formed along the rest of the four sides.

A stopper protrusion contacting a side surface of the cover plate coupled to the base plate may be formed on a middle portion of the opening region. A height from a surface of the base plate to the guide holder may be greater than a thickness of the cover plate.

The groove for receiving the flat panel display may be formed on each of top and under surfaces of the base plate, the opening region may be formed on each of the top and under surfaces, the guide holder may be formed on each of the top and under surfaces, and a pair of the base plates may be respectively fitted on the top and under surfaces of the base plate by the sliding motion.

The opening region formed on the top surface of the base plate may be located at an opposite side to the opening region formed on the undersurface of the base plate. The base plate and the cover plate may be formed of synthetic resin.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
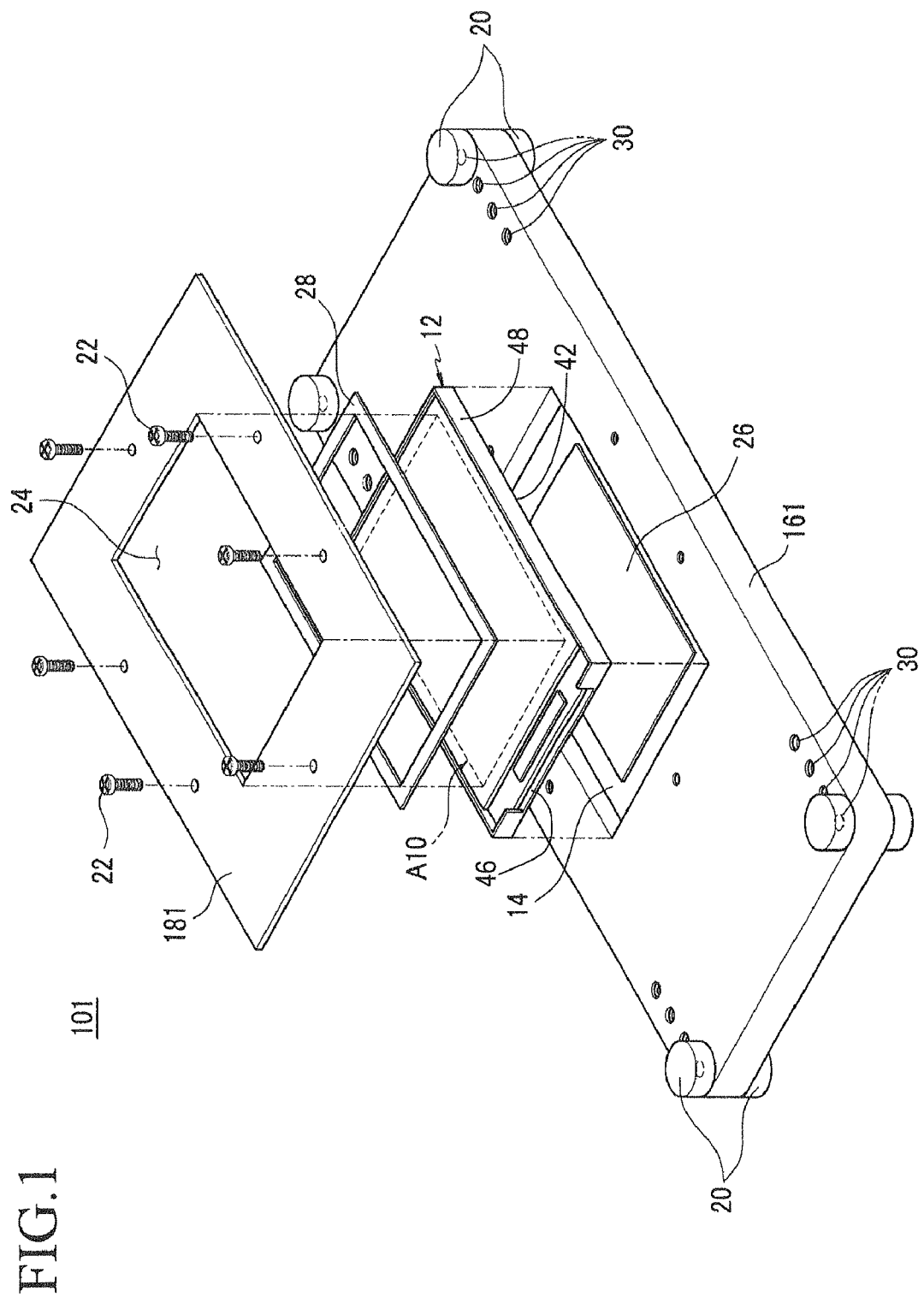
FIG. 1 is an exploded perspective view of a jig frame for a drop test of a flat panel display according to a first exemplary embodiment of the present invention.
Figure 2:
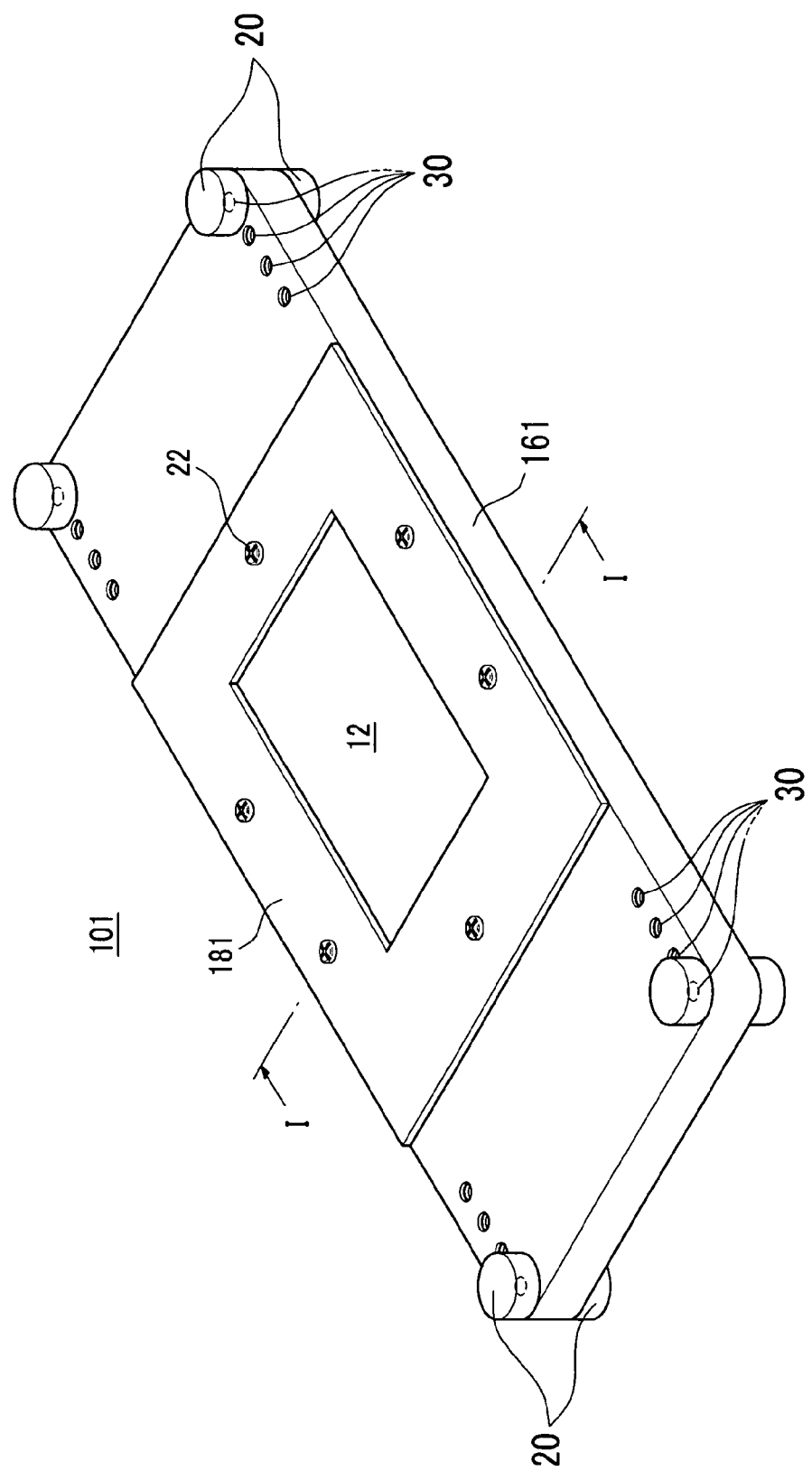
FIG. 2 is a perspective view of the jig frame of FIG. 1, when it is assembled.
Figure 3:
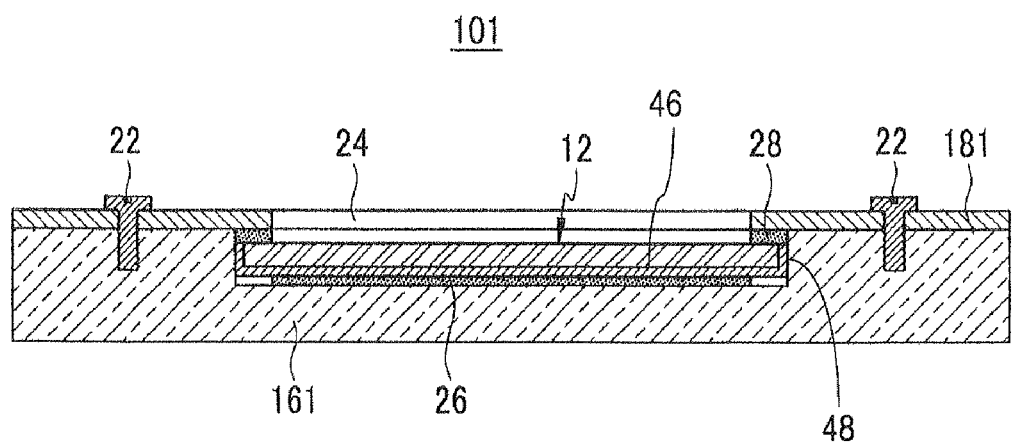
FIG. 3 is a cross-sectional view taken along line I-I of FIG. 2.

The following will describe a jig frame for a drop test of a flat panel display according to a first exemplary embodiment of the present invention with reference to FIGS. 1 to 3.

Referring to FIGS. 1 to 3, a jig frame 101 of the first exemplary embodiment includes a base plate 161 having a groove 14 for receiving a flat panel display 12 and a cover plate 181 overlapping the flat panel display 12 and base plate 161 and fixing the flat panel display 12. The cover plate 181 is coupled to the base plate 161. Balance weights 20 are installed on an edge of the base plate 161.

The base plate 161 may be formed in a rectangular shape having a pair of long sides and a pair of short sides. The base plate 161 may be formed of synthetic resin that can provide flexibility. The base plate 161 is formed to be relatively thin so that it can be easily deformed during the drop test. For example, when a thickness of the flat panel display is 2 mm or less, a thickness of the base plate 161 may be about 4 mm.

The groove 14 for receiving the flat panel display 12 is formed on a center of the base plate 161. When the flat panel display 12 is formed in the rectangular shape having the pair of long sides and the pair of short sides, the flat panel display 12 may be received in the groove 14 such that long sides thereof can be disposed in parallel with the long sides of the base plate 161.

The cover plate 181 overlaps the flat panel display 12 and base plate 161 and is screw-coupled to the base plate 161 by at least four screws 22. Like the base plate 161, the cover plate 181 is also formed of synthetic resin. For example, the cover plate 181 is formed of transparent synthetic resin such as polycarbonate so that the flat panel display 12 installed in the jig frame 101 is visible to the naked eye.

The cover plate 181 may be provided with an opening having the same size as a display region A10 of the flat panel display 12. If the opening 24 is not formed, it may be difficult to precisely identify fine cracks formed on the display region A10 due to the reflection of external light from the cover plate 181. Therefore, the opening 24 enables the tester to precisely identify even the fine cracks formed on the display region A10.

In FIGS. 1 and 2, the base plate 161 and the cover plate 181 are screw-coupled to each other by six screws 22, the number of the screws 22 is not limited to this configuration. Additionally, other coupling members may be used instead of the screws.

A double-sided adhesive tape 26 may be disposed between the base plate 161 and the flat panel display 12 to fix the flat panel display 12 to the base plate 161. A shock absorption tape 28 may be located between the cover plate 181 and the flat panel display 12 to prevent the surface damage of the flat panel display 12 by the contact with the cover plate 181.

The balance weights 20 are located at four corners of the base plate 161. The balance weights 20 are installed on the top and under surfaces of each of the corners of the base plate 161. That is, eight balance weights 20 may be installed on the base plate 161. Each of the balance weights 20 may be formed of a cylindrical metal body having a predetermined diameter and height. That is, the balance weights 20 protrude from the top and under surfaces of the base plate 161.

By the weight and protruding height of each of the balance weights 20, the jig frame 101 may significantly induce the deformation of the base plate 161 so that, when the jig frame 101 drops on a test floor, the flat panel display 12 installed in the jig frame 101 can have the similar dynamic movement to a case where it is mounted on an actual electronic device.

The balances weights 20 are fixed on the base plate 161 by being fitted in coupling holes (or grooves) 30 formed on the base plate 161. That is, at least two coupling holes 30 are arranged in a length direction of the base plate 161 at each corner of the base plate 161 so that the mounting location of the balance weights 20 is adjustable. In FIGS. 1 and 2, four coupling holes 30 are exemplarily arranged at each corner of the base plate 161.

Figure 4:
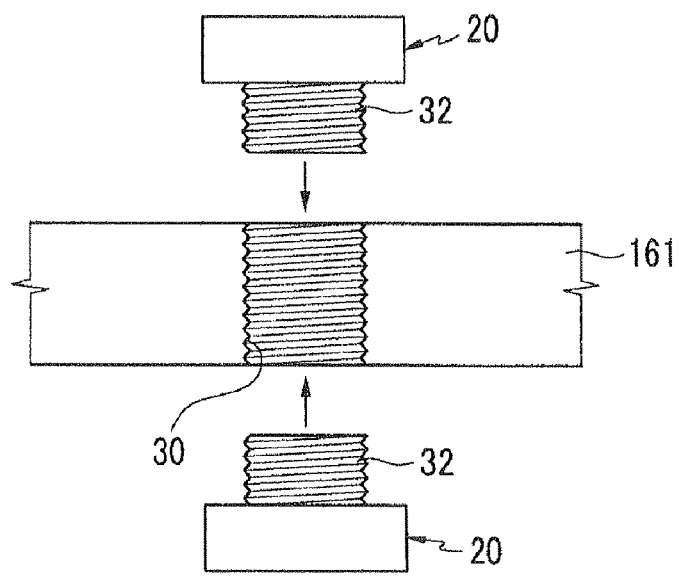
FIG. 4 is an exploded perspective view of a base plate and balance weights that are depicted in FIG. 1.

FIG. 4 is an exploded perspective view of the base plate and balance weights. Referring to FIG. 4, each of the coupling holes 30 formed through the base plate 161 is provided with a female thread and each of the balance weights 20 is provided at a surface facing the base plate 161 with a coupling portion 32 having a male thread. Therefore, the balance weight 20 can be fixed on the base plate 161 as the coupling portion 32 is screw-coupled to the coupling hole 30. A coupling structure of the base plate 161 and the balance weight 20 is not limited to the above configuration but may be variously modified.

Referring again to FIGS. 1 to 3, the jig frame 101 of the present exemplary embodiment may have a variety of balance weights 20 having different weights (e.g., 100 g, 130 g, and 150 g) in accordance with the weight of the electronic device to which the flat panel display will be installed. That is, by varying the weight of each of the balance weights 20, the weight of the jig frame 101 can be adjusted.

Further, by adjusting the mounting location of each of the balance weights 20, a degree of deformation occurring at a central portion of the jig frame 101 can be easily controlled. That is, when the jig frame 101 drops on the test floor, the central portion of the jig frame 101 in which the flat panel display 12 is installed is deformed. At this point, the degree of deformation occurring at the central portion of the jig frame 101 can be adjusted by varying the mounting location of the balance weights 20 along the long sides of the base plate 161.

As described above, by varying the weight and mounting location of each of the balance weights 20, the weight of the jig frame 101 and the degree of deformation of the base plate 161 can be controlled. As a result, the jig frame 101 can meet a variety of conditions of the electronic device in which the flat panel display 12 will be installed.

Figure 5:
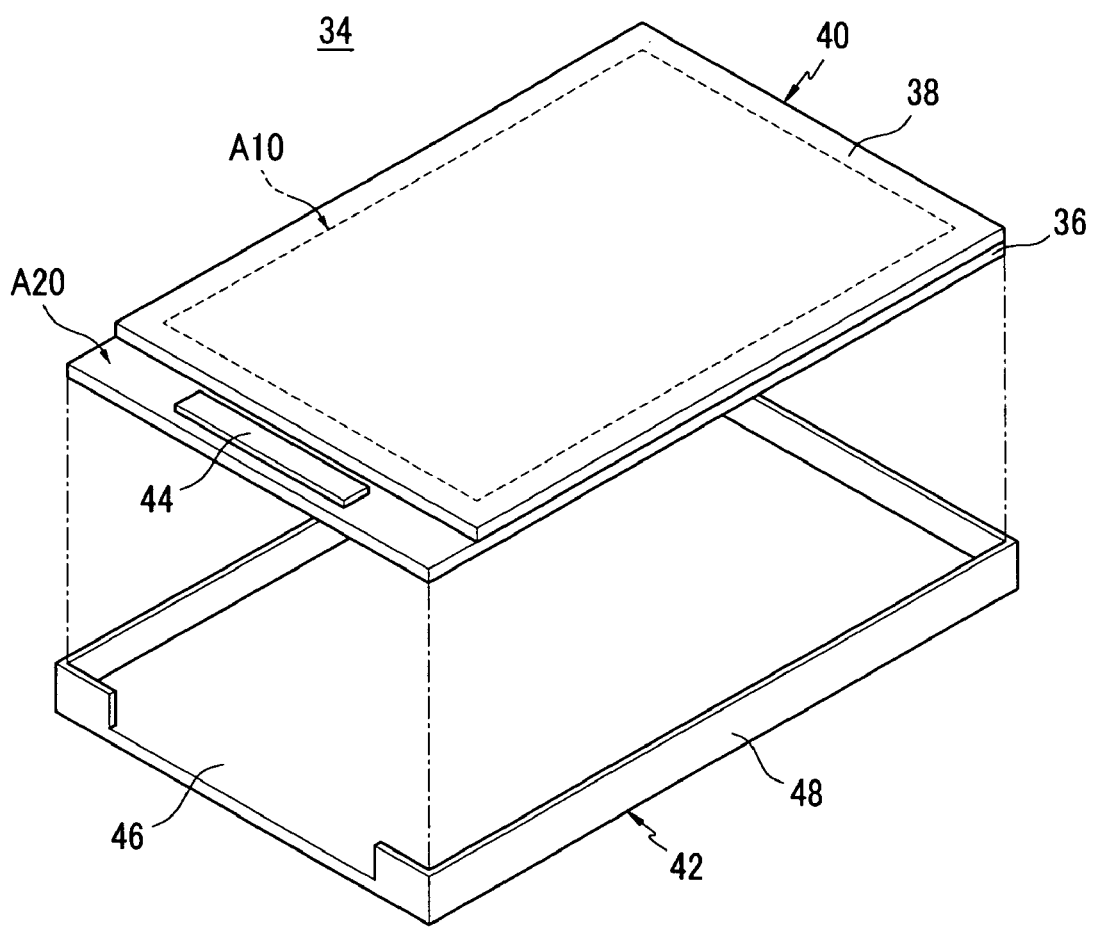
FIG. 5 is an exploded perspective view of an OLED display.

The flat panel display 12 installed in the above-described jig frame 101 may be an OLED display. FIG. 5 is a perspective view of an OLED display. Referring to FIG. 5, an OLED display 34 includes a panel assembly 40 and a bezel 42 coupled to the panel assembly 40 at a rear side of the panel assembly 40. The panel assembly 40 includes first and second substrates 36 and 38 that are coupled to each other by sealant. OLEDs are formed in a display region A10 of the panel assembly 40.

A plurality of sub-pixels is disposed in a matrix pattern at the display region A10 of the first substrate 36. Pad electrodes (not shown) for transferring electric signals to the sub-pixels are disposed at the pad region A20 of the first substrate 36. In FIG. 5, the reference number 44 indicates an integrated circuit chip that is installed on the pad region A20 through a chip-on-glass (COG) process.

The bezel 42 includes a bottom portion 46 on which the panel assembly 40 is disposed and at least one sidewall 48 that extends from at least one side edge of the bottom portion 46 to the panel assembly 40 to face a side surface of the panel assembly 40. The bezel 42 is coupled to the panel assembly 40 to serve to enhance mechanical strength of the panel assembly 40.

Figure 6:
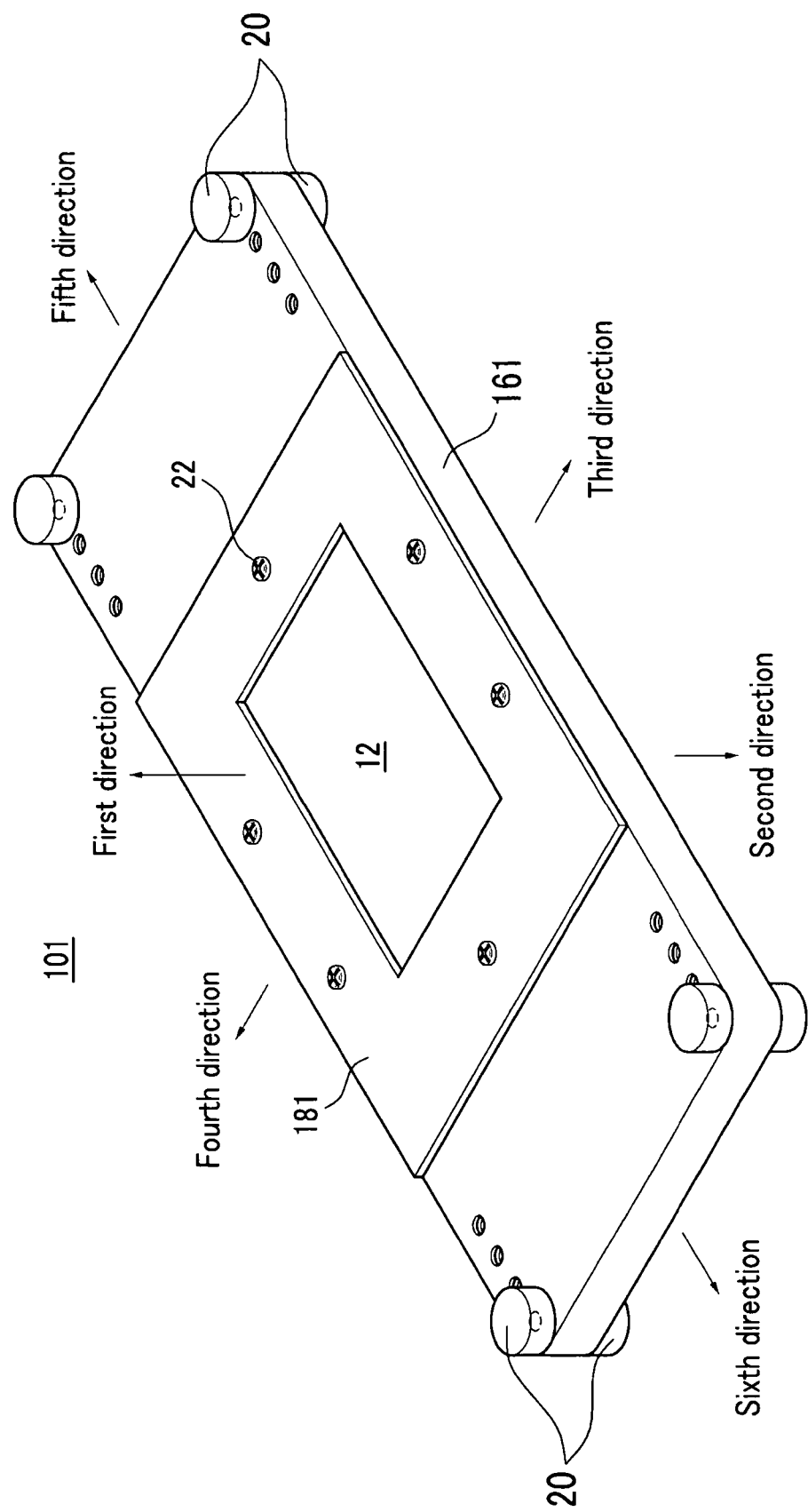
FIG. 6 is a schematic diagram illustrating dropping directions of the jig frame of FIG. 2.

FIG. 6 is a schematic diagram illustrating dropping directions of the jig frame shown in FIG. 2. Referring to FIG. 6, the jig frame 101 drops in six different directions (first to sixth directions) corresponding to six side surfaces thereof to test durability of the flat panel display 12.

In the drop test, the flat panel display 12 may be broken by impact energy and/or by excessive deformation thereof. When the actual electronic device on which the flat panel display 12 is installed drops, the flat panel display 12 is broken by a combination of the impact energy and the excessive deformation.

In accordance with the present exemplary embodiment, the jig frame 101 is designed to transfer impact energy to the flat panel display 12 and induces the deformation of the flat panel display 12 due to the deformation of the base plate 161. Therefore, like the actual electronic device, the jig frame 101 can apply the combination of the impact energy and the deformation energy to the flat panel display 12.

The jig frame 101 of the present exemplary embodiment is very durable. In addition, after the jig frame 101 drops on the test floor, the tester can immediately identify if the flat panel display 12 is damaged by observing the flat panel display 12 through the transparent cover plate 181 and the opening 24 of the cover plate 181 without disassembling the jig frame 101.

Figure 7:
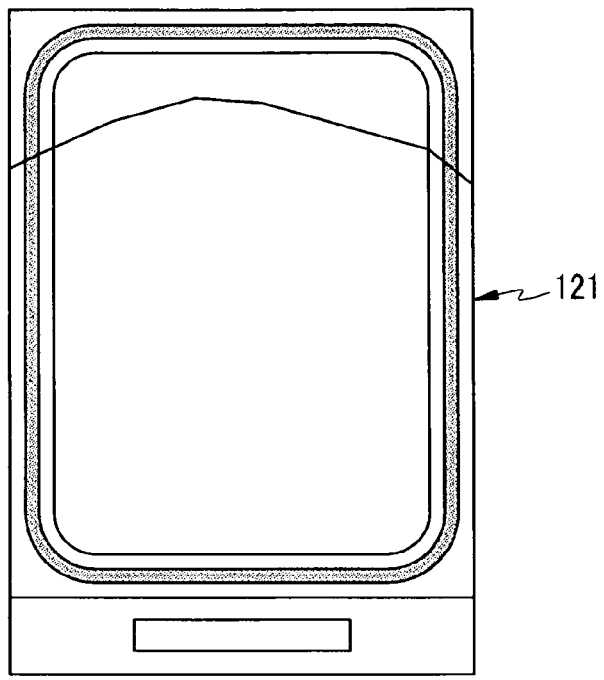
FIGS. 7 to 9 are schematic diagrams illustrating broken states of flat panel displays in drop tests performed by using the jig frame of FIG. 1.
Figure 8:
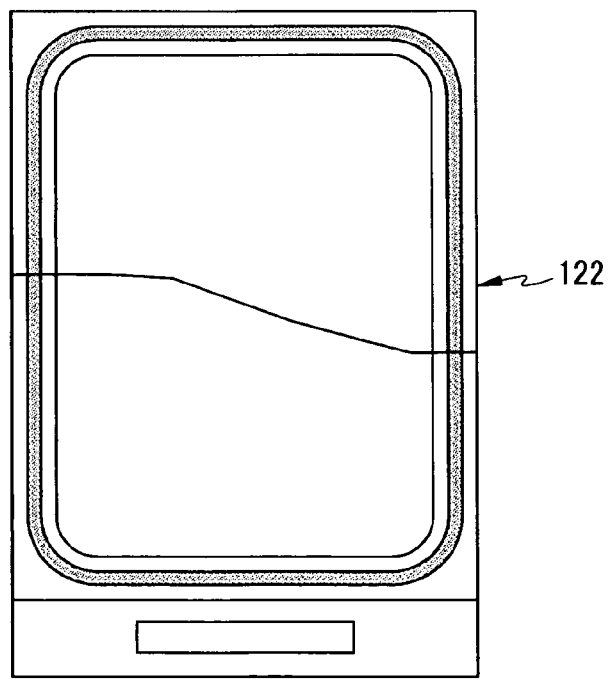
Figure 9:
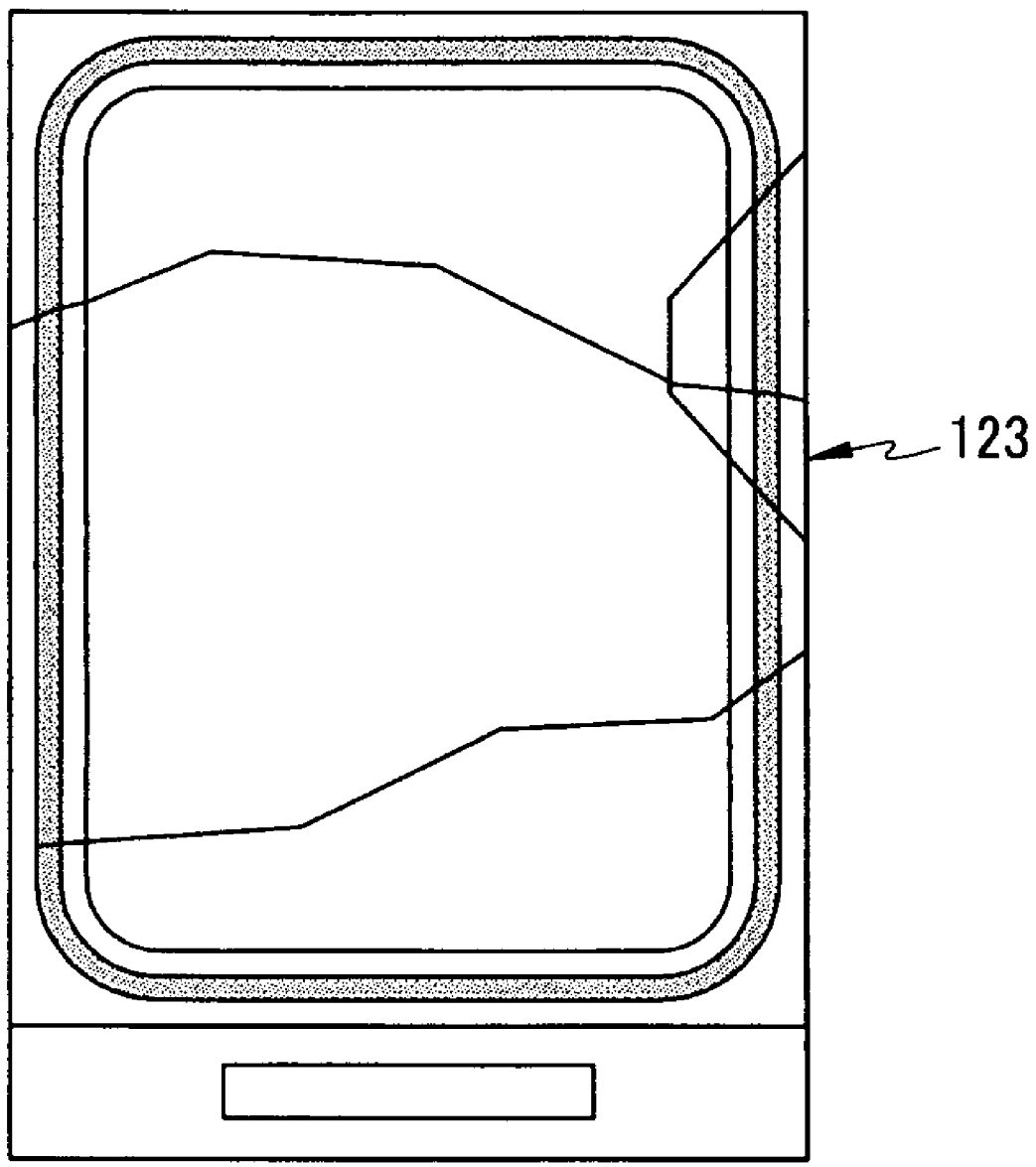

FIGS. 7 to 9 are schematic diagrams illustrating broken states of flat panel displays in the drop tests performed by using the jig frame of FIG. 1.

Referring to FIGS. 7 to 9, flat panel displays 121, 122, and 123 were broken by cracks formed in a transverse direction (i.e., a width direction). This result is similar to a result of a test that is performed using actual electronic devices in which the respective flat panel displays 121, 122, and 123 are installed. Therefore, it can be noted that the drop test using the jig frame 101 of the present exemplary embodiment is effective and available.

Figure 10:
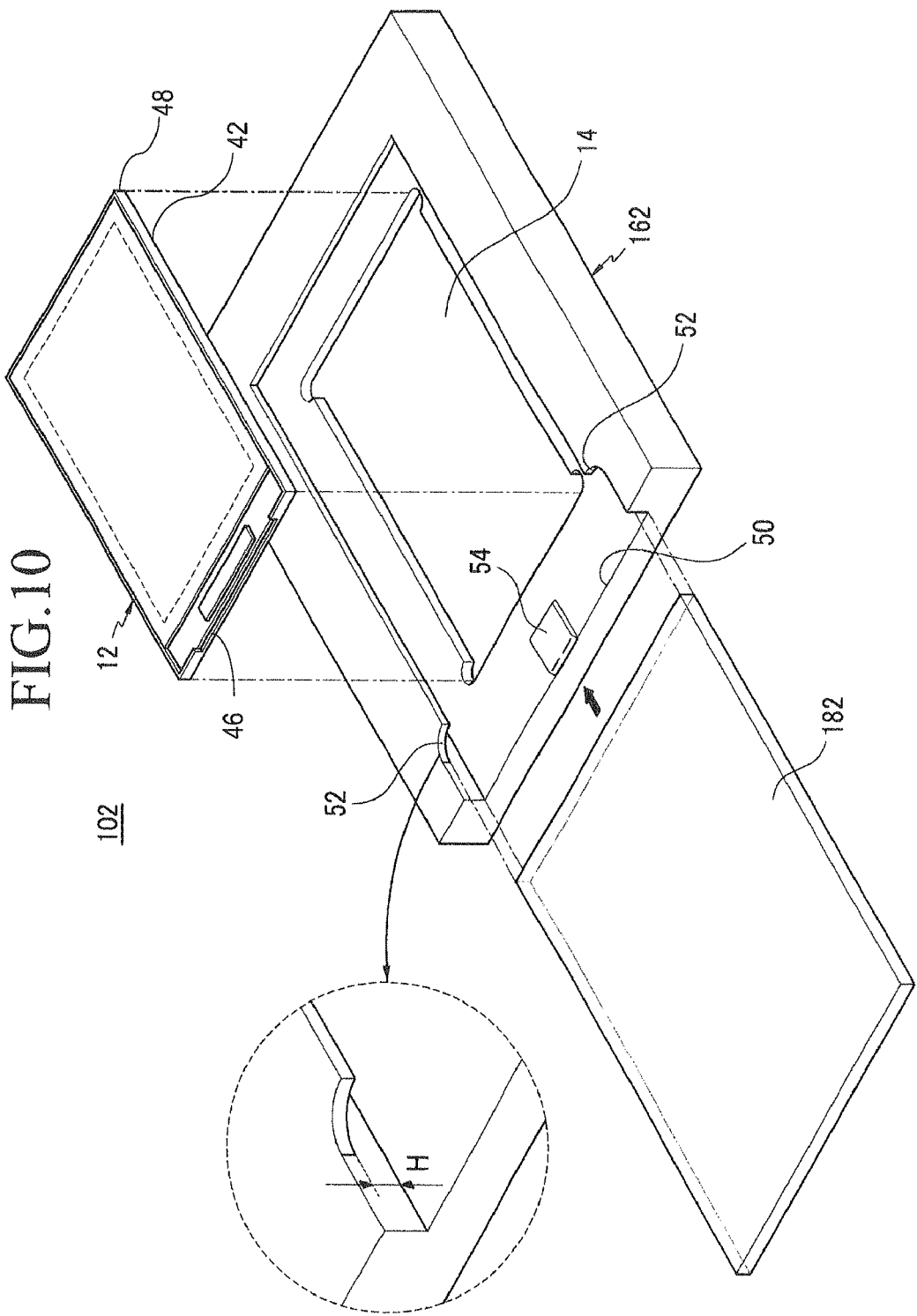
FIG. 10 is an exploded perspective view of a jig frame for a drop test of a flat panel display according to a second exemplary embodiment of the present invention.
Figure 11:
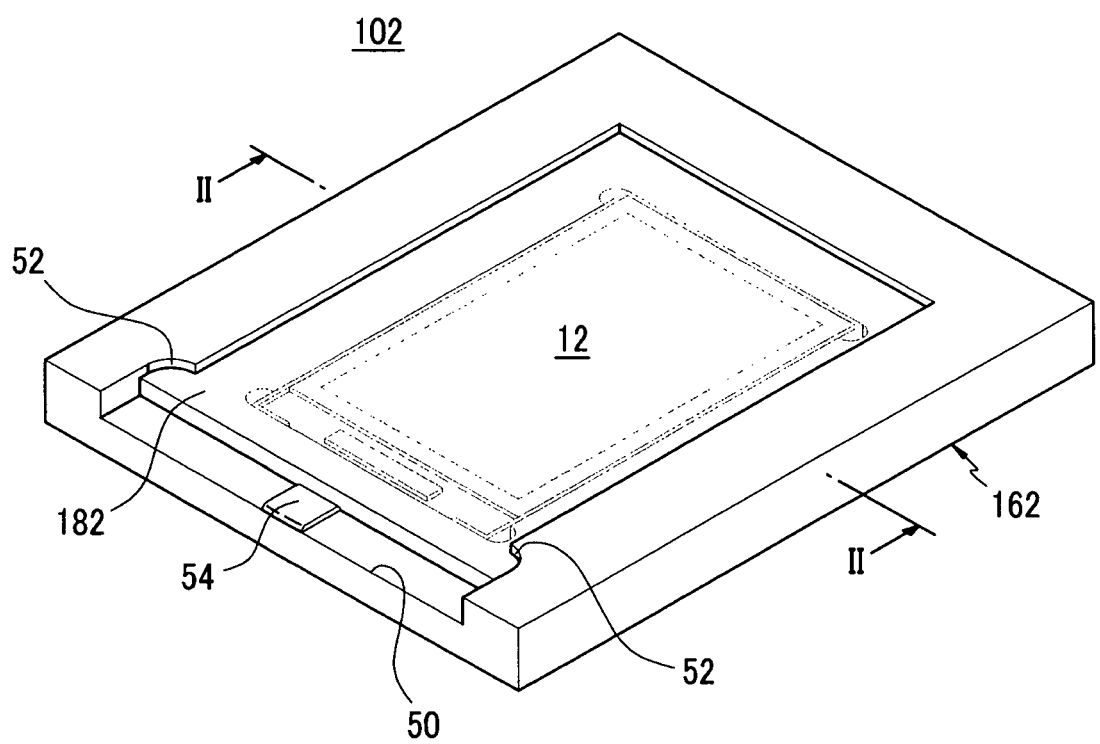
FIG. 11 is a perspective view of the jig frame of FIG. 10, when it is assembled.
Figure 12:
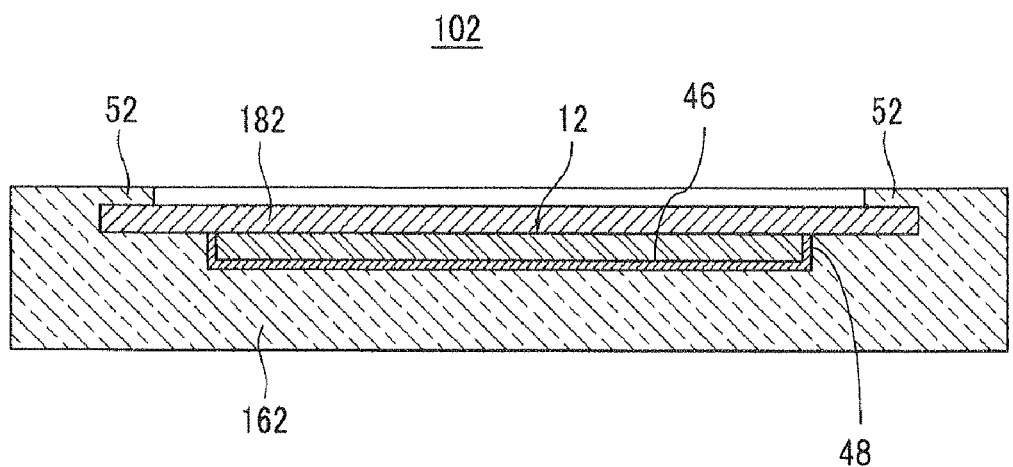
FIG. 12 is a cross-sectional view taken along line II-II of FIG. 11.

The following will describe a jig frame for a drop test of a flat panel display according to a second exemplary embodiment of the present invention with reference to FIGS. 10 to 12.

Referring to FIGS. 10 to 12, a jig frame 102 of the second exemplary embodiment includes a base plate 162 having a groove 14 for receiving the flat panel display 12 and a cover plate 182 that slides into the base plate 162 to fix the flat panel display 12 by overlapping the flat panel display 12.

The base plate 162 may be formed in a rectangular shape having a pair of long sides and a pair of short sides. The cover plate 182 may be also formed in a rectangular shape having a pair of long sides and a pair of short sides. The base plate 162 and the cover plate 182 may be formed of synthetic resin that can provide flexibility. The groove 14 for receiving the flat panel display 12 is formed on a center of the base plate 162 and is slightly larger than the flat panel display 12 so that the flat panel display 12 can be easily received in and separated from the groove 14.

The base plate 162 is provided at one of sides with an opening region 50 through which the cover plate 182 slides into the base plate 162. A guide holder 52 is formed along the rest of the sides of the base plate 162. The guide holder 52 is elevated from a surface of the base plate 162 by a predetermined height H (see FIG. 10).

The height H from the surface of the base plate 162 to the guide holder 52 is slightly greater than a thickness of the cover plate 182 considering a sliding margin of the cover plate 182. The cover plate 182 is coupled to the base plate 162 by sliding into a space defined between the guide holder 52 and the surface of the base plate 162. At this point, the guide holder 52 partly overlaps an edge of the cover plate 182.

In FIGS. 10 and 11, the opening region 50 is exemplarily formed at one of the short sides of the base plate 162 and the guide holder 52 is formed along the long sides and the other of the short sides. However, the location and shape of the guide holder 52 are not limited to the above-described configuration. That is, the location and shape of the guide holder 52 may be variously modified.

A stopper protrusion 54 may be formed on a middle portion of the opening region 50 through which the cover plate 182 slides into the base plate 162. When the cover plate 182 is completely fitted in the base plate 162, the stopper protrusion 54 contacts a side surface of the cover plate 182 to prevent the cover plate 182 from being separated from the base plate 162. Therefore, the separation of the cover plate 182 from the base plate 162 can be prevented during the drop test. The structure of the stopper protrusion 54 is not specifically limited but variously modified.

As in the first exemplary embodiment, the cover plate 182 is also formed of transparent synthetic resin. As the cover plate 182 is formed of the transparent synthetic resin, the flat panel display 12 installed in the jig frame 102 is visible to the naked eye.

Figure 13:
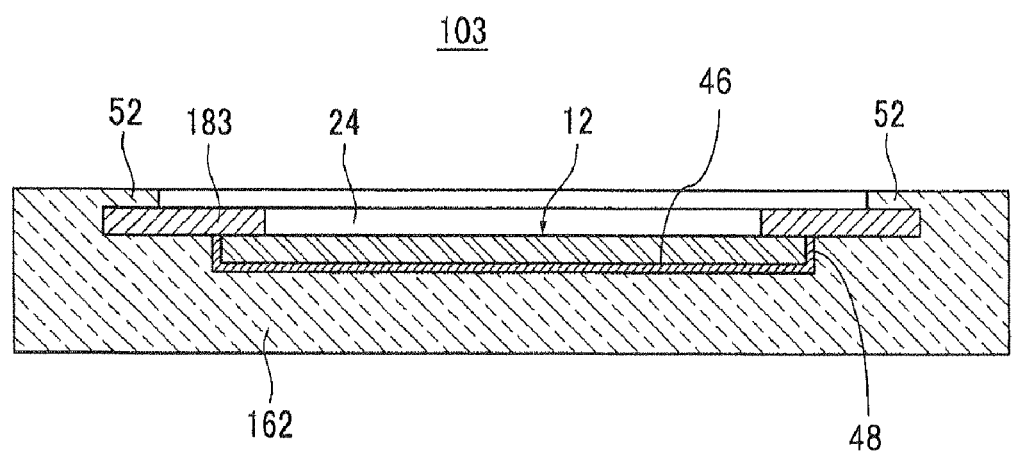
FIG. 13 is a cross-sectional view of a jig frame for a drop test of a flat panel display according to a third exemplary embodiment of the present invention.

The following will describe a jig frame for a drop test of a flat panel display according to a third exemplary embodiment of the present invention with reference to FIG. 13.

Referring to FIG. 13, a jig frame 103 of the present exemplary embodiment is substantially identical to the jig frame of the second exemplary embodiment except that an opening 24 is formed on a cover plate 183. The opening 24 formed on the cover plate 183 is formed to correspond to a display region of a flat panel display 12. The opening 24 has the same size as the display region. The tester can precisely identify even fine cracks of the flat panel display 12 through the opening 24 of the cover plate 183.

Figure 14:
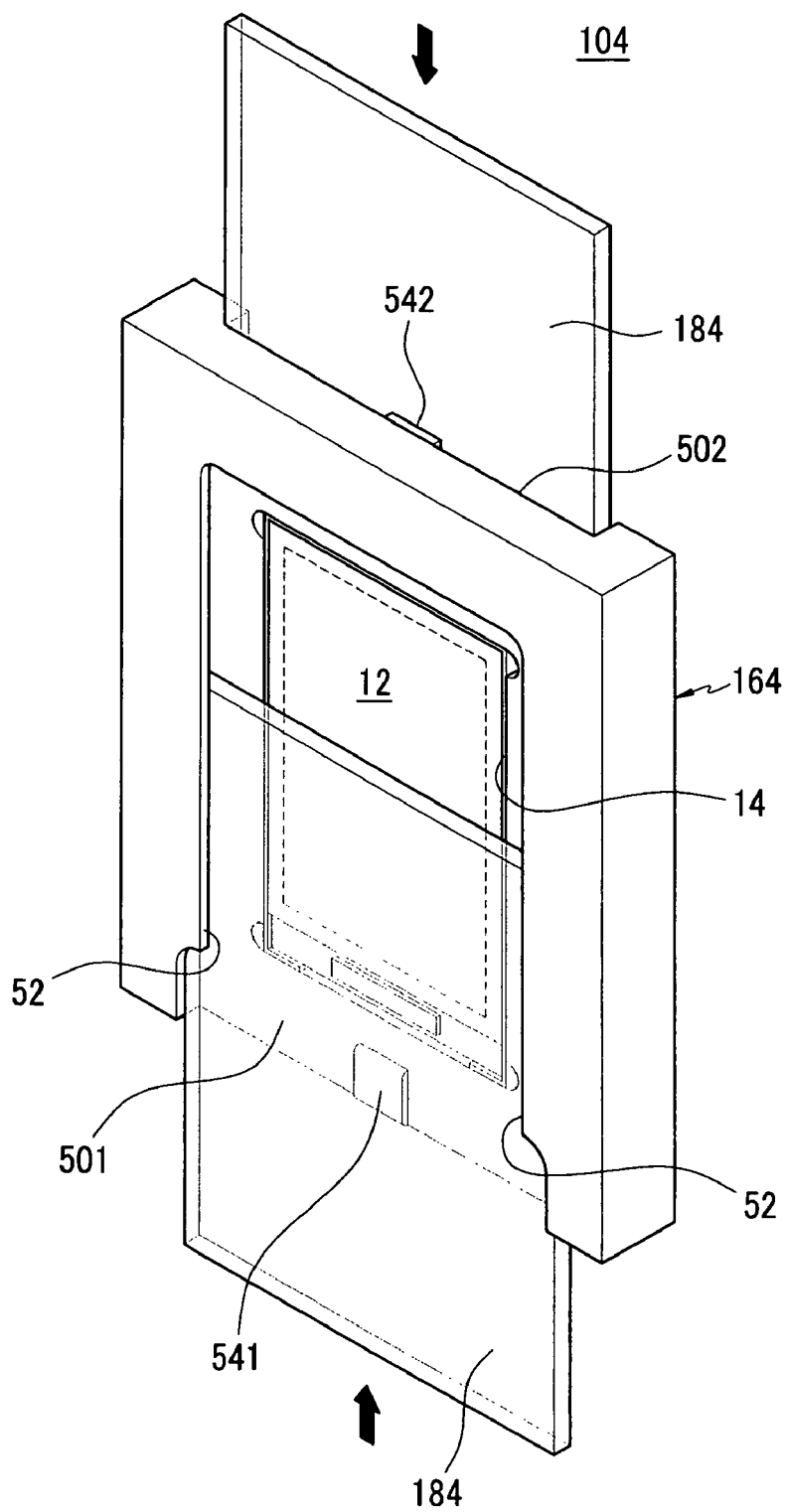
FIG. 14 is an exploded perspective view of a jig frame for a drop test of a flat panel display according to a fourth exemplary embodiment of the present invention.
Figure 15:
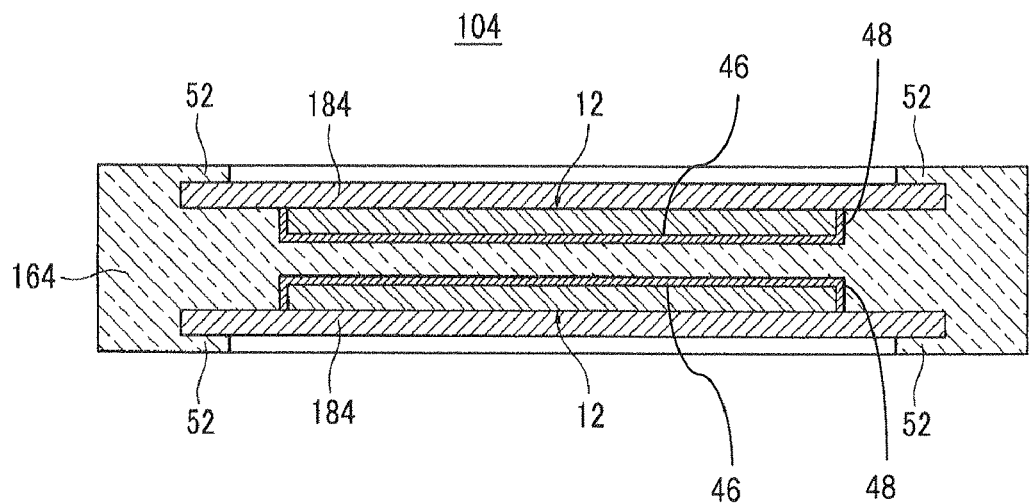
FIG. 15 is a cross-sectional view of the jig frame of FIG. 14, when it is assembled.

The following will describe a jig frame for a drop test of a flat panel display according to a fourth exemplary embodiment of the present invention with reference to FIGS. 14 to 15.

Referring to FIGS. 14 and 15, a jig frame 104 the present exemplary embodiment is substantially same as the jig frame of the second exemplary embodiment except that grooves 14 for respectively receiving flat panel displays 12 are formed on respective opposite surfaces (i.e., top and under surfaces) of the base plate 164, guide holders 52 are formed on the respective opposite surfaces of the base plate 164, and a pair of cover plates 184 are respectively coupled to the opposite surfaces of the base plate 164.

An opening region 501 and stopper protrusion 541 of the top surface of the base plate 164 may be formed at an opposite side to an opening region 502 and stopper protrusion 542 of the under surface of the base plate 164. That is, when the opening region 501 and stopper protrusion 541 are formed on a portion of the top surface of the base plate 164, which is close to one of a pair of short sides of the base plate 164, the opening region 502 and stopper protrusion 542 may be formed on a portion of the under surface of the base plate 164, which is close to the other of the pair of short sides. Such a symmetric structure of the jig frame 104 prevents a weight of the jig frame 104 from being concentrated in one direction.

According to the above-described configuration of the jig frame 104 of the present exemplary embodiment, two flat panel displays 12 can be installed in one jig frame 104. Therefore, two flat panel displays 12 can be drop-tested simultaneously and thus the test time can be effectively reduced.

Figure 16:
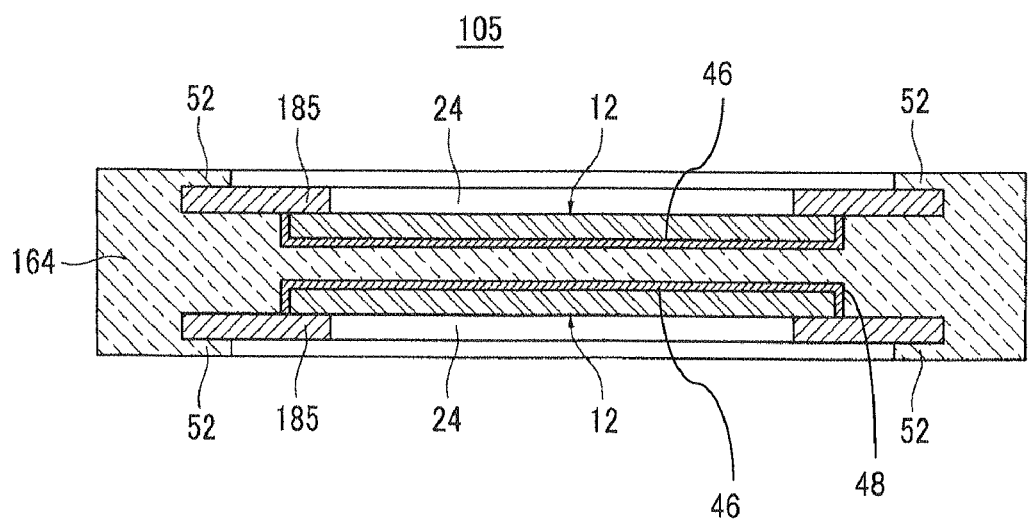
FIG. 16 is a cross-sectional view of a jig frame for a drop test of a flat panel display according to a fifth exemplary embodiment of the present invention.

The following will describe a jig frame for a drop test of a flat panel display according to a fifth exemplary embodiment of the present invention with reference to FIG. 16.

Referring to FIG. 16, a jig frame 105 of the present exemplary embodiment is identical to the jig frame of the fourth exemplary embodiment except that openings 24 are formed on respective cover plates 185. Since the shape and function of the opening 24 formed on each of the cover plates 185 are same as those of the opening of the third exemplary embodiment, detailed description thereof will be omitted herein.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A jig frame for a drop test of a flat panel display device, the jig frame comprising:
a base plate having a groove for receiving the flat panel display device; and
a cover plate fixing the flat panel display device by covering the flat panel display device and being coupled to the base plate,
wherein the cover plate is formed of transparent material so that the flat panel display device installed in the jig frame is visible to outside of the cover plate, the base plate is formed in a rectangular shape, and a balance weight is located at each of four corners of the base plate, and
wherein an opening region through which the cover plate slides into the base plate is formed on one of four sides of the base plate, and a guide holder partly overlapping the cover plate and coupled base plate is formed along the rest of the four sides.

2. The jig frame of claim 1, wherein the flat panel display device comprises a display region and the cover plate is provided with an opening corresponding to the display region.

3. The jig frame of claim 1, further comprising at least one balance weight coupled to an edge of the base plate.

4. The jig frame of claim 1, wherein the base plate is provided at each of the four corners with a plurality of coupling holes arranged in a lengthwise direction of the base plate and the balance weight at each of the four corners is coupled to one of the coupling holes.

5. The jig frame of claim 4, wherein each of the coupling hole is provided with a female thread and the balance weight is provided with a male thread so that the balance weight is screw-coupled to the coupling hole.

6. The jig frame of claim 1, wherein the balance weight is provided on each of top and under surfaces of each of the four corners of the base plate.

7. The jig frame of claim 6, wherein the balance weight provided on the top surface of the base plate has the same weight as the balance weight provided on the under surface of the base plate.

8. The jig frame of claim 1, wherein the cover plate is coupled to the base plate by insertion of the cover plate into the base plate by sliding motion.

9. The jig frame of claim 1, wherein a stopper protrusion contacting a side surface of the cover plate coupled to the base plate is formed on a middle portion of the opening region.

10. The jig frame of claim 1, wherein a height from a surface of the base plate to the guide holder is greater than a thickness of the cover plate.

11. The jig frame of claim 1, wherein the groove for receiving the flat panel display device is formed on each of top and under surfaces of the base plate, the opening region is also formed on each of the top and under surfaces, the guide holder is also formed on each of the top and under surfaces, and a pair of the base plates are respectively fitted on the top and under surfaces of the base plate by the sliding motion.

12. The jig frame of claim 11, wherein a stopper protrusion contacting a side surface of the cover plate coupled to the base plate is formed on each of a middle portion of the opening regions respectively formed on the top and under surfaces of the base plate.

13. The jig frame of claim 11, wherein a height from the top surface of the base plate to the guide holder formed on the top surface of the base plate is greater than a thickness of the cover plate fitted on the top surface of the base plate and a height from the under surface of the base plate to the guide holder formed on the under surface of the base plate is greater than a thickness of the cover plate fitted on the under surface of the base plate.

14. The jig frame of claim 1, wherein the opening region formed on the top surface of the base plate is located at an opposite side to the opening region formed on the under surface of the base plate.

15. The jig frame of claim 1, wherein the base plate and the cover plate are formed of synthetic resin.

16. A jig frame for a drop test of a flat panel display device, the jig frame comprising:
   a base plate having a groove for receiving the flat panel display device;
   a cover plate fixing the flat panel display device by covering the flat panel display device and being coupled to the base plate; and
   a display region contained in the cover plate for unobstructed viewing of the flat panel display device,
   wherein the cover plate is formed of transparent material so that the flat panel display device installed in the jig frame is visible to outside of the cover plate, the base plate is formed in a rectangular shape, and a balance weight is located at each of four corners of the base plate, and
   wherein an opening region through which the cover plate slides into the base plate is formed on one of four sides of the base plate, and a guide holder partly overlapping the cover plate and coupled to the base plate is formed along the rest of the four sides.

17. The jig frame of claim 16, wherein said display region is an opening in which no transparent material is present.

18. A jig frame for a drop test of a flat panel display device, the jig frame comprising:
   a rectangular base plate having a groove receiving the flat panel display device; and
   a rectangular transparent cover plate fixing the flat panel display device by covering the flat panel display device, and at least three sides of the cover plate being physically coupled to the base plate,
   wherein a balance weight is located at each of four corners of the rectangular base plate and
   wherein an opening region through which the cover plate slides into the base plate is formed on one of four sides of the base plate, and a guide holder partly overlapping the cover plate and coupled to the base plate is formed along the rest of the four sides.

* * * * *